United States Patent [19]

De Villez

[11] Patent Number: 4,591,602

[45] Date of Patent: * May 27, 1986

[54] OZONIDE ESTERS AND TOPICAL COMPOSITIONS CONTAINING SAME

[75] Inventor: Richard L. De Villez, New Braunfels, Tex.

[73] Assignee: James H. Brown, Scottsdale, Ariz.

[ * ] Notice: The portion of the term of this patent subsequent to May 29, 2001 has been disclaimed.

[21] Appl. No.: 601,537

[22] Filed: Apr. 18, 1984

Related U.S. Application Data

[63] Continuation-in-part of Ser. No. 369,163, Apr. 16, 1982, Pat. No. 4,451,480.

[51] Int. Cl.⁴ ........................................... A61K 31/335
[52] U.S. Cl. ........................................ 514/463; 514/714
[58] Field of Search ............... 424/278, 338; 549/431; 514/463, 714

[56] References Cited

U.S. PATENT DOCUMENTS

| | | | |
|---|---|---|---|
| 2,083,572 | 6/1937 | McKee | 539/431 |
| 2,356,062 | 8/1944 | Johnson | 424/76 |
| 3,504,038 | 3/1970 | Beal | 549/431 X |
| 4,451,480 | 5/1984 | De Villez | 424/278 |

OTHER PUBLICATIONS

The Merck Index, 9th ed., 1976, p. 15117.

*Primary Examiner*—Leonard Schenkman
*Attorney, Agent, or Firm*—Wolder, Gross & Yavner

[57] ABSTRACT

A novel compound, and stable compositions thereof for the effective, nonirritating treatment of microbial colonization are disclosed. The compound is used for the topical treatment of affected areas as well as for control of certain diarrheas. The compound is the ozonide of the liquid wax jojoba oil. The ozonide material of the present invention has the ability to release nascent oxygen directly to locales to at least inhibit the microorganisms without the characteristic dryness and skin irritation associated with previous benzoyl peroxide treatments. The compositions are stable, in contrast to the limited shelf-stability of the previously used benzoyl peroxide formulation. This ozonide and products containing same have no tendency to become rancid, which is a problem with other ozonides.

8 Claims, No Drawings

OZONIDE ESTERS AND TOPICAL COMPOSITIONS CONTAINING SAME

This application is a continuation-in-part of my invention filed as application Ser. No. 369,163, on Apr. 16, 1982 and now U.S. Pat. No. 4,451,480 issued May 29, 1984 and entitled THERAPEUTIC COMPOSITION AND METHOD.

FIELD OF THE INVENTION

The present invention relates to topical compositions containing oil-soluble ozonized compounds prepared by ozonizing unsaturated oils, esters, alcohols, ethers and fatty acids, containing olefinic linkages and specifically jojoba oil. More particularly the invention relates to compositions containing such oil-soluble ozonides, preferably containing the novel jojoba ozonide for the effective non-irritating treatment of acne and related microbial infestations and infections.

BACKGROUND OF THE INVENTION

As mentioned in the parent application, previous acne treatments were based upon the topical treatment of the lesions with benzoyl peroxide. Benzoyl peroxide compositions upon hydrolysis, on contact with tissue fluids or under adverse storage conditions, release oxygen and form benzoic acid. The latter is a strong keratolytic agent, irritating and drying the skin and causing exfoliation. In acne the skin is sensitive and sensitized. Such heroic insults can be avoided by the use of the present invention.

In my original application, I described the method of treating acne and related topical skin conditions caused by microbial infestations comprising the topical application of ozonides of an olefin of the formula

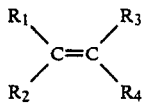

wherein:
$R_1$ or $R_2$ may be hydrogen or:

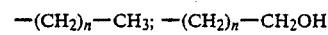

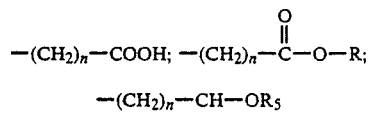

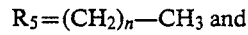

where
$R_5 = (CH_2)_n—CH_3$ and
$n =$ an integer from 0 to 12;
with $R_3$ and $R_4$ being any value given for $R_1$ and $R_2$ with the proviso that $R_1$ and $R_2$ cannot both equal H and also $R_3$ and $R_4$ cannot both equal H.

Specifically mentioned were the ozonides of olive oil, sesame oil, castor oil, peanut oil and jojoba oil. The ozonides of these unsaturated fixed oils from animal and vegetable sources: olive, sesame, corn and peanut oils, are based on the regular food and fixed oils that are glyceryl esters of the naturally occurring mixed fatty acids in the range $C_{14}$ to $C_{18}$. Olive oil for example contains about 25% tristearin, 75% triolein, and about 5% trilinolein. The other glyceryl esters contain more or less the same fatty acid glycerides but in different proportions. Castor oil is slightly different in that it also contains the glyceryl ester of a hydroxy acid of similar chain length. It is primarily glyceryl triricinoleate. Ricinoleic acid is a hydroxyoleic acid.

Jojoba oil differs from all of the above in that it is a wax, albeit, a liquid wax, i.e., one mole of a long chain olefinic fatty alcohol esterified with one mole of a long chain olefinic fatty acid. It is composed almost entirely of esters of high molecular weight ($C_{18-24}$), straight chain monoethylenic acids and monoethylenic alcohols, for example, erucyl 11-cis-eicosenoate of the formula—$CH_3(CH_2)_7CH=CH(CH_2)_{12}$—O—$CO(CH_2)_9CH=CH(CH_2)_7CH_3$.

These unsaturated acids are a mixture of cis-11-eicosenoic ($C_{20}$) and cis-13-docosenoic ($C_{22}$) erucic, with small quantities of oleic ($C_{18}$) and nervonic ($C_{24}$) acids. The unsaturated alcohols are a mixture of cis-11-eicosenol, cis-13-docosenol and cis-15 tetrocosenol, with small quantities of alcohols of lower molecular weight. Note that all the alcohols and acids are primarily of the cis configuration.

The conventional position for a double bond in other natural fats or oils composed of $C_{18}$ acids is $\Delta 9$ i.e. between carbon 9 and 10 of each of the fatty acids, but jojoba oil has mainly $\Delta 11$ and $\Delta 13$ unsaturation in the alcohols and acids, because of the large amount of $C_{20}$ and $C_{22}$ chains. All of the jojoba monoenes can be placed in the $\omega$-9 acids or $\omega 9$ alcohols homologous series.

In the method aspects of the allowed parent application the acne lesions are contacted with the above-mentioned oil and wax derived ozonides. These, on contact with the sebaceous secretions, hydrolyze to liberate nascent oxygen and the triglyceride base oil and its fractions. The oxygen destroys, or at least inhibits the growth of any anaerobic bacteria and other microbial acne infection sources and the base oil residue acts as a liquifying emollient.

However the ozonide of the glyceryl esters are not very stable. The glyceryl ester ozonides, i.e., vegetable oil ozonides, are all liquid at ambient temperature and have stability periods that are inadequate for commercial distribution and use purposes. In the presence of light and even traces of moisture the glyceryl oil-based ozonides break down releasing the oxygen which also oxidizes the ozone-opened olefinic linkages, breaking the long chain to shorter chain fractions of shorter chain fatty acids ($C_{6-10}$) and oxidized ketones of the fatty glycerides. As a result, rancidity develops creating very objectionable odors.

THE INVENTION

Jojoba oil, by contrast to the above described materials, when subjected to the Harries Ozonide two-stage reaction (Merck Index 9th Ed.—Section of Organic Name Reactions, page ONR-40) is ozonized at the olefinic linkages on both the alcohol and acid moieties. The first reaction proceeds according to the equation:

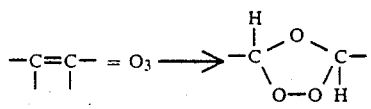

under conditions to be more fully discussed hereafter.

The jojoba ozonide is a cosmetically elegant cream/paste which, while oily (like petrolatum), does not feel uncomfortably greasy on the skin. Additionally, the jojoba ozonide alters the skin's micro-environment by delivery of nascent oxygen on contact with the tissue. This reduces microbial infection and enhances the skin's healing ability and healing rate. At the same time, the films on the skin formed by the long chain residues of the fatty alcohol-fatty acid ester prevent moisture loss through the skin and allow the stratum corneum to remain hydrated thus alleviating dry skin.

In addition to the above noted uses for the ozonides of fixed oils and waxes for the treatment of topical infections and colonization as in acne, it must be noted that beneficial results have been reported from the instillation of gaseous ozone in certain other conditions.

Specifically, it was reported in Science (V 209, pages 931-933 (1980)) that 0.3 to 0.8 parts per million of gaseous ozone in air selectively inhibits cultures of human cancer cells from lung, breast and uterine tumors, in a controlled comparative study.

Careful application of the ozonides and preferably jojoba ozonide may prove useful, after ranging experiments indicate comparative concentrations of ozonide to ozone useful for such tissue inhibition. Similarly, certain viruses, such as, specifically, type 1 poliovirus, have been inactivated and killed by contact with ozone. (Appl. Environ-Microbial. V 37 (1979) 715-718). Ozonized jojoba should have similar effects on viral cultures.

Ozone has been instilled into or flowed over various bodily orifices or surfaces to treat varicose ulcerations, hepatitis, arthritis, sinusitis, colitis, diarrhea in children, rectal problems, vaginitis, etc. (Public: 6th Ozone Wld, Cong. Proceed. Washing.D.C. May 23-26, 1983) and it is proposed to replace the irritating gaseous ozone with jojoba ozonide as providing better control of concentration and more effective contact during application.

The novel compound, jojoba ozonide, is prepared by the ozonization of pure jojoba oil by an ozone source. Several commercial laboratory and industrial ozone sources are available including a laboratory size ozonizer manufactured by Union Carbide Co. furnishing ozone containing oxygen at about 0.5 ft.$^3$/min. (20,000 ppm $O_3$) and industrial ozonizers manufactured by Ozone Research and Equipment Corp. capable of furnishing about 500 pounds of ozone per day. The resulting ozonized jojoba product does not become rancid. This is in contrast to the ozonides of the triglycerides of the fatty acids. Preferably, the ozone gas used for preparing the ozonides and preferably the jojoba ozonide of this invention is manufactured from medicinal grade oxygen, i.e., Oxygen U.S.P.

By using the pure oxygen source, instability and irritation noted in ozone gas mixtures and ozonides, prepared from ozonized air and believed caused by nitrogen oxides formed in the high voltage ozonizers, is avoided. Nitrogen oxides are extremely irritating to the skin as they form nitrous and nitric acids on hydration. The use of Oxygen U.S.P. as feed material to the ozonizer avoids the formation of such nitrogen oxides.

During the manufacture, the ozone gas is introduced below the jojoba oil surface via a fritted glass sparger. The ozonizing reaction is exothermic. It is preferred to keep the reactor temperature in the range 35°-65° C. and preferably at about 50°±5°. At lower than 35° C. the ozone uptake is too slow and some non-utilized ozone may vent from the reactor. (As ozone is an irritant inhalant, classified as hazardous, vented ozone should be fed through a hypo bath and decomposed.)

At 50° C. the ozone is quantitatively absorbed until the weight gain of the jojoba oil is 13.8%.

A ratio of 1.2 to 1.25 gms. of ozone are required to produce a 1.0 gram weight increase in jojoba oil (pharmaceutical grade). This reaction efficiency is attained when the temperature during ozonolysis is controlled to 50°±5°. This is a simple matter as the reaction is exothermic. The reaction rate is controlled by the ozone gas feed rate. A simple water-cooled vessel is adequate even in reaction vessels ozonizing 300-325 gallons of oil (one ton) daily.

It is important to maintain the temperature of the ozonized oil and the reactor below 97° C. At 90°-100° C. a rapid and potentially dangerous oxidation of ozonized jojoba oil, in the presence of oxygen, takes place. For this reason and since the optimum reaction rate is met at about 50° C., an arbitrary safe temperature limit for the ozonization reaction is in the range 45°-60° C. and preferably 50° C.±5° C. This is easily maintained on an industrial scale. To manufacture one ton of completely ozonized jojoba oil (13.8% weight gain) 307 gallons of jojoba oil are treated with 380 lbs. of ozone. With a 1.2-1.25 utilization factor, the weight gain of 13.8% requires 304 pounds of ozone. Any off-gases are fed to a hypo bath for OSHA safety and GMP procedures.

The completely ozonized oil (13.8% weight gain) or 11.5% $O_3$ by iodometric assay, while useful, is too concentrated for most topical uses. Experimental ranging indicates that it may be usefully diluted and marketed for OTC compounding at about 5.0-12% $O_3$ (iodometrically) nominally 10% as ozonide. Useful diluents are jojoba oil and/or jojoba oil isomerates, i.e., transisomerized jojoba oil, jojoba hydrogenates and blends thereof. The isomerates of jojoba oil are marketed as Jojobutter® 51 and 31. They are isomorphous and of buttery consistency at room temperature. Jojoba hydrogenates are semi-crystalline materials useful for providing a hardened to solid consistency where required.

As the above mentioned jojoba oil and its derivatives are essentially anhydrous they are useful stable diluents for the jojoba ozonide. Anhydrous diluents are desired as the presence of moisture promotes premature hydrolysis of the ozonide.

Other useful anhydrous diluents or compounding materials for preparing compatible and cosmetically acceptable vehicles for the jojoba ozonide are 1,2-dimethylethane, ethyl acetate, cyclohexane, dioxane, Petrolatum Liquid USP, and cosmetic grades of mineral oil petrolatum, ozokerite, squalane, polydimethylcyclosiloxane (Dow Corning Silicone Fluids #344 and 345), acetone, MEK, paraffin waxes and similar stable anhydrous oxidation-resistant materials.

A general guide line for compounding of cosmetically acceptable vehicles for jojoba ozonide is to include only oxidation-resistant, anhydrous materials such as have been used in the past as vehicle components for benzoyl peroxide and hydroquinone. In addition to the diluents mentioned above, the polyalkoxylated fatty ethers (CTFA) are good solubilizing agents for jojoba oils, are miscible therewith and are stable in the presence of oxidants. These include the polyethyleneglycol- and polypropyleneglycol-ethers with various fatty alcohols. They are marketed with various amounts of ethylene or propylene oxide per mole of the ether and are CTFA listed. Also useful are the various synthetic lanolins and lanolin esters, as these commercially available materials have considerable stability in the presence of oxidizers. These are also listed in the CTFA handbook and directory.

In the course of developing methods for preparing the jojoba ozonide and diluting it before formulation, a simple method for determining the degree of reaction and the amount of ozonide in jojoba oil has been developed based on the changes in the refractive index of the jojoba oil and jojoba ozonide mixtures. Pure jojoba oil has a refractive index (m 46°) 1.4573±0.0002. The completely ozonized oil (11.5% by idometric titration) has a refractive index at 46° C. of 1.4540. There is a straight line relationship between these points, thus permitting following the reaction by the refractive index.

It also provides a simple assay for jojoba ozonides diluted in the isomerates or in the oil.

Another method has recently been developed for following the ozonization of jojoba oil. It is based on the classical method for location of carbon-carbon double bonds in aliphatic systems. Ozone is reacted to form a stable ozonide containing the characteristic five-membered ozonide ring at the former site of the double bond. The reaction proceeds stochiometrically with formation of polyozonides as the molecule is polyunsaturated.

In jojoba oil, which has a monesteric system (in contrast to the common edible vegetable oils which are triglycerides) the oil is principally docos-13-enyl eicos-11-enoate, a di-unsaturated ester, thus capable of forming a diozonide.

Hydrolysis by treating with Zn and acetic acid yielded nonal-1-al of the formula:

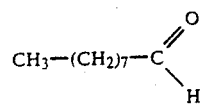

having a retention time of 6.8 minutes and a di-aldehyde ester of the formula:

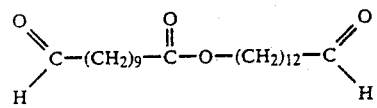

having a retention time of 5.7 minutes. The ester linkage was often also disrupted.

Because the dialdehyde ester is the predominant reaction product, it can be assumed for the assay that the diozonide is the predominant ozonide product. As the method does not distinguish between the aldehydic acid and the aldehydic alcohol, quantitation is based on the quantitative presence and peak height of the dialdehydic ester (supra). The cleavage is quantitative and the degree of ozonization of the jojoba oil can be quantitatively determined by the peak height of the dialdehyde formed by this method.

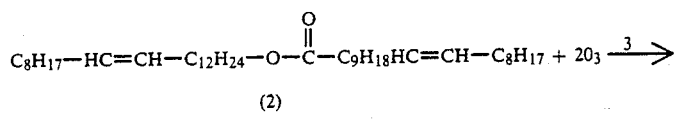

(2)

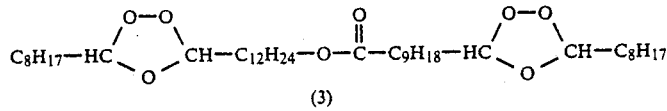

(3)

HPLC with a Bechman 100A Pump operating at 1.0 ml/min. using a dichlormethane mobile phase on a column of μ-Spherogel 50A, 300 mm 8.0 mm on the hydrolized ozonized sample shows emergence of a high molecular-weight peak at approximately 3.9 minutes. Pure jojoba oil elutes at about 4.1 minutes. In all cases, the height of the 3.9 minute peak varied directly with the ozone content of parent material (iodometric).

For assay purposes, hydrolysis of the ozonide is promoted by reacting the ozonide with zinc metal and acetic acid. The five-membered ring is dehydrated and rearranged to form the aldehyde of the fractions attached to the respective portions of the cleaved ring:

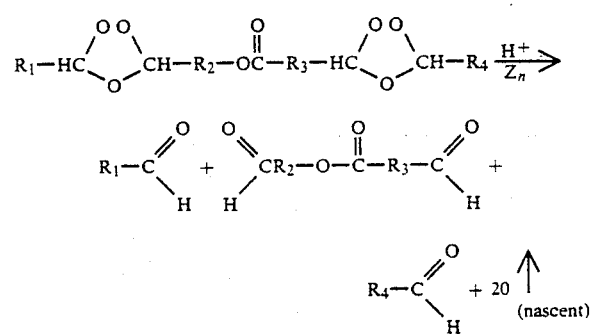

In preparing topical preparations of jojoba ozonides for commercial use, the jojoba ozonide should be contained in an anhydrous vehicle. The presence of water initiates hydrolysis of the ozonide portion of the molecule resulting in the release of nascent oxygen. For special situations as at surgical sites, the ozonide may be admixed with hydrous vehicles or medicaments containing such vehicles immediately prior to application. This hydrolysis reaction is not rapid. Nascent oxygen is slowly released from the ozonide over a period of more than six hours after contact with moisture as the rate of the hydrolysis reaction is controlled by the rate of diffusion of the water into the oleaginous ozonide.

The nascent oxygen is more rapidly released on contact with the skin. This hydrolysis reaction is catalyzed by the peroxidase enzymes normally present on the skin. Thus, the release of nascent oxygen in situ in antimicrobial amounts from topical compositions is assured.

For assurance of the release of sufficient amounts of nascent oxygen, at sites of microbial colonization, for the control of such colonies to below infectious levels, it is useful for the jojoba ozonide to be present in applied films in a concentration of at least 0.1% by weight. In the control of active infections including anaerobic organisms, much higher concentrations of the jojoba ozonide, up to the full 11.4% (iodoemetric) concentration of $O_3$ in the jojoba ozonide is desirable. Sufficient for cosmetic treatment and control of acne are jojoba ozonide concentrations in the range 0.5 to 10% with about 2 to 10% being preferred for commercial over-the-counter (OTC) preparations.

In the formulation, the ozonide may be supplied in semi-liquid emulsion, creamy, paste or semi-solid or solid consistency. The less viscous products can be applied by cotton pledgets or cotton-tipped applicators. The creams or pastes can be packaged in jars or tubes for direct application by the fingers or pledgets. The semi-solids can be prepared in stick form as in theatrical grease paint, cover sticks or lip balms and is similarly applied by abrasive contact. The solidified jojoba ozonide can be formulated into dusting powder or into suppositories, melting at body temperature, for appropriate application into orifices or to ulcers as required.

The invention will be further described in the Examples appended below. It is to be noted that the examples merely reflect currently preferred formulations used in screening for various uses. While the examples reflect fully useful products, they have not been presented as reflecting commercial products with all the necessary cosmetic elegance required in the marketplace, including colorants, odorants, as well as viscosity control agents and similar materials. It is, of course, understood that the invention is directed to jojoba ozonides and formulations containing such ozonides in compatible, anhydrous, cosmetically-acceptable vehicles.

EXAMPLES

Example 1

In this formulation, the solvency of acetone that is commonly used in acne preparations is incorporated into the ozonide-containing formula.

| Ingredient | Parts by Weight |
|---|---|
| Jojoba Oil Ozonide (4.4%) | 15.0 |
| Acetone | 15.0 |
| Dow Corning #344 Silicone Fluid (Polydimethylcyclosiloxane) | 68.8 |
| Menthol | 0.2 |

The resultant clear solution is cosmetically elegant and can be applied with the fingers or various types of applicators. Alternatively, it can be conveniently packaged on towlette material in a foil package or cotton-tip applicators.

Example 2

| Ingredient | Parts By Weight |
|---|---|
| Jojoba Oil Ozonide (4.4%) | 20.0 |
| Isopropyl Palmitate | 15.0 |
| Isopropyl Alcohol | 64.5 |
| Menthol | 0.5 |

This example demonstrates an alcohol-containing, "invisible" composition that can be applied as in Example 1.

The following formulations are liquids suitable for application with sponge-type or roll-on applicators but are also suitable for finger or applicator packaging.

Example 3

| Weight % | Ingredient |
|---|---|
| 33% | C$_{12-15}$ Alcohols Benzoate (Finetex) |
| 13% | Jojoba Oil Ozonide (4.4%) |
| 54% | 344 Silicone Fluid (Dow Corning) |

Example 4

| Weight % | Ingredient |
|---|---|
| 25% | Jojobutter ®-31 |
| 25% | Jojoba Oil Ozonide (4.4%) |
| 50% | Acetone |

Example 5

| Weight % | Ingredient |
|---|---|
| 35% | Neobee M-5 (vegetable triglycerides) |
| 20% | Jojoba Oil Ozonide (8%) |
| 45% | 345 Silicone Fluid (Dow Corning) |

Example 6

| Weight % | Ingredient |
|---|---|
| 10% | Jojoba Oil Ozonide (11.8%) |
| 60% | Acetone |
| 30% | Robane (Squalene) |

The following formulation is a gel suitable for packaging in a jar, tubes or in the above applicators.

Example 7

| Ingredient | Weight % |
|---|---|
| Fumed Silica (Silicone Dioxide) | 10% |
| Mineral Oil, Light | 30% |
| 344 Silicone Fluid | 15% |
| Jojoba Oil Ozonide 11.8% | 25% |
| C$_{12-15}$ Alcohols Benzoate | 20% |

The following formulation is an example of a spot-balm that can be packaged in a "stick" or small jar.

Example 8

| | Weight % |
|---|---|
| Phase I | |
| JOJOBA OIL OZONIDE (11.8%) | 20.0% |
| BENTONE GEL M10 | 20.0% |
| PROPOPET ALBA | 20.0% |
| JOJOBUTTER ®-51 | 15.0% |
| CARNATION OIL | 18.9% |
| PARAFFIN WAX 125/130 | 5.0% |
| Phase II | |
| D & C RED #17 (0.05% SOL. in CARNATION OIL) | 1.0% |
| Phase III | |
| PERFUME | 0.1% |
| | 100.0% |

Procedure
1. Heat Phase I to 70° C. and mix until homogeneous.

2. Add the color of Phase II to a portion of Phase I (approximately 3 parts) and mix until completely dispersed. Add this portion to the balance of Phase I.

3. Add the perfume of Phase III, mix until completely dispersed and empty into storage containers. When molding the batch melt the contents of an entire storage container because separation in this storage container can occur.

Example 9

|  | Weight % |
|---|---|
| Isopropyl Lanolate | 7.000 |
| Jojobutter ®-31 | 3.000 |
| Oleyl Alcohol | 9.700 |
| Beeswax | 13.500 |
| Esbesco Wax | 13.500 |
| Ozokerite | 4.000 |
| Propyl Paraben | 0.150 |
| Butyl Paraben | 0.150 |
| Castor Oil | 3.000 |
| PPG-30 Lanolin Ether | 30.000 |
| Jojoba Ozonide (11.8%) | 14.000 |
| Colorants and Odorants | 1.200 |
| Molt into sticks | 100.000 |

Example 10

Vaginal or Rectal Suppositories

|  | Weight % |
|---|---|
| Jojoba Oil Ozonide (11.8%) | 30% |
| Jojobutter ® 51 | 70% |
|  | 100% |

The melt is cast into a suppository mold. The suppositories melt in the range 38°–46° C.

What is claimed is:

1. Jojoba ozonide of refractive index $n^{46°} = 1.4540$.

2. The jojoba ozonide according to claim 1 dissolved in anhydrous jojoba oil, its anhydrous isomers and/or hydrogenates or mixtures thereof.

3. Composition for the control of microbial infections which comprise an effective amount of the jojoba ozonide according to claim 1 in an anhydrous vehicle.

4. Composition according to claim 3 containing at least 0.1% of the jojoba ozonide.

5. Composition according to claim 3 for the control of topical conditions caused by microbial colonization which comprises control-effective amounts of jojoba ozonide in the range 0.5% to 11.8% $O_3$ (by iodometry).

6. The composition according to claim 4 wherein said vehicle includes an anhydrous diluent for said jojoba ozonide selected from the group consisting of jojoba oil, transisomerized jojoba oil, hydrogenated jojoba oil and isomorphous mixtures thereof.

7. The composition according to claim 5 wherein the concentration of said jojoba ozonide is in the range 2–10 wt.% $O_3$.

8. The method for treating topical microbial infections which comprises the step of applying topically to an affected area an effective amount of a composition according to claim 3.

* * * * *